United States Patent
Kleczewski

(10) Patent No.: US 10,191,001 B2
(45) Date of Patent: *Jan. 29, 2019

(54) CONVEYOR-BELT SYSTEM FOR MEASURING CONDITIONS THAT VARY THE RESONANT FREQUENCY OF A RESONANT CIRCUIT

(71) Applicant: Laitram, L.L.C., Harahan, LA (US)

(72) Inventor: Lazlo Kleczewski, Oostzaan (NL)

(73) Assignee: Laitram, L.L.C., Harahan, LA (US)

(*) Notice: Subject to any disclaimer, the term of this patent is extended or adjusted under 35 U.S.C. 154(b) by 216 days.

This patent is subject to a terminal disclaimer.

(21) Appl. No.: 14/974,890

(22) Filed: Dec. 18, 2015

(65) Prior Publication Data

US 2016/0103084 A1    Apr. 14, 2016

Related U.S. Application Data

(63) Continuation-in-part of application No. 14/253,577, filed on Apr. 15, 2014, now Pat. No. 9,476,757.

(51) Int. Cl.
*B65G 17/30* (2006.01)
*G01N 27/02* (2006.01)
(Continued)

(52) U.S. Cl.
CPC .......... *G01N 27/028* (2013.01); *B65G 17/08* (2013.01); *B65G 17/30* (2013.01); *B65G 43/02* (2013.01);
(Continued)

(58) Field of Classification Search
CPC .. G01N 27/028; G01N 27/023; G01N 27/228; B65G 17/08; B65G 17/30;
(Continued)

(56) References Cited

U.S. PATENT DOCUMENTS 3,332,506 A    7/1967    Bradfield
3,565,195 A *  2/1971    Miller ............ G01G 7/06
                                                177/210 R
(Continued)

FOREIGN PATENT DOCUMENTS

JP    1998-002782 A    1/1998
JP    2000249591 A    9/2000
(Continued)

OTHER PUBLICATIONS

International Search Report and Written Opinion of the International Searching Authority, PCT/US2016/064432, dated Mar. 16, 2017, Korean Intellectual Property Office, Republic of Korea.
(Continued)

*Primary Examiner* — Randy Gibson
(74) *Attorney, Agent, or Firm* — James T. Cronvich

(57) ABSTRACT

A conveyor belt and a sensing system for sensing various conditions on a conveyor belt. The belt includes an array of sensing elements embedded in the belt to measure belt conditions. The sensing elements form parts of passive resonant circuits that each include a capacitor and an inductive coil. The capacitor or the inductive coil can be a sensing element. Measuring circuits external to the belt are inductively or capacitively coupled to the resonant circuits in the belt as they pass closely by. The sensing elements change the resonant frequency of their resonant circuits as a function of the sensed conditions. Frequency detectors in the measuring circuits measure that frequency change and convert it into a functionally related value used to determine a belt condition. Exemplary conditions include temperature, pressure, humidity, spillage, and product weight.

24 Claims, 14 Drawing Sheets

(51) Int. Cl.
*G01N 27/22* (2006.01)
*G01D 5/12* (2006.01)
*G01L 1/14* (2006.01)
*G01G 19/00* (2006.01)
*G01G 11/04* (2006.01)
*B65G 43/02* (2006.01)
*G01L 5/10* (2006.01)
*B65G 17/08* (2006.01)
*G01G 19/03* (2006.01)
*G01G 7/02* (2006.01)
*G01G 7/06* (2006.01)
*G01D 5/243* (2006.01)

(52) U.S. Cl.
CPC .............. *G01G 7/02* (2013.01); *G01G 7/06* (2013.01); *G01G 19/035* (2013.01); *G01L 1/14* (2013.01); *G01L 1/144* (2013.01); *G01L 5/101* (2013.01); *G01N 27/023* (2013.01); *G01N 27/228* (2013.01); *G01D 5/243* (2013.01)

(58) Field of Classification Search
CPC . B65G 43/02; G01G 7/02; G01G 7/06; G01G 19/035; G01G 11/003; G01G 11/04; G01L 1/14; G01L 1/144; G01L 5/101; G01D 5/243
See application file for complete search history.

(56) References Cited

U.S. PATENT DOCUMENTS

| | | | |
|---|---|---|---|
| 3,643,753 A | 2/1972 | Godwin et al. | |
| 3,656,137 A * | 4/1972 | Ratz | B65G 43/02 198/810.02 |
| 3,678,378 A * | 7/1972 | Trott | G01G 7/06 177/210 C |
| 3,742,477 A * | 6/1973 | Enabnit | B65G 43/02 198/810.02 |
| 3,875,481 A * | 4/1975 | Miller | G01G 7/06 361/283.1 |
| 4,520,885 A * | 6/1985 | Jeffrey | G01G 3/12 177/210 C |
| 4,629,851 A | 12/1986 | Holle | |
| 4,663,589 A | 5/1987 | Fiori, Jr. | |
| 4,825,967 A | 5/1989 | Sakamoto et al. | |
| 4,856,603 A | 8/1989 | Murakoso et al. | |
| 5,219,032 A | 6/1993 | Keen | |
| 5,349,183 A | 9/1994 | Barkhoudarian | |
| 5,359,154 A | 10/1994 | Tsukasa et al. | |
| 5,898,298 A | 4/1999 | Brandsma et al. | |
| 5,942,991 A | 8/1999 | Gaudreau | |
| 6,323,452 B1 | 11/2001 | Bonnet | |
| 6,376,784 B1 | 4/2002 | Morinaka | |
| 6,588,574 B2 | 7/2003 | Koini et al. | |
| 7,036,653 B2 | 5/2006 | Reznik et al. | |
| 7,494,004 B2 * | 2/2009 | Stolyar | B65G 43/02 198/810.02 |
| 7,635,060 B2 | 12/2009 | Lagneaux | |
| 9,004,271 B2 * | 4/2015 | Fourney | G01G 11/003 198/502.2 |
| 9,146,146 B2 | 9/2015 | Laird et al. | |
| 2002/0145529 A1 * | 10/2002 | Kuzik | B65G 43/02 340/676 |
| 2004/0149049 A1 * | 8/2004 | Kuzik | B65G 43/02 73/862.453 |
| 2005/0007239 A1 | 1/2005 | Woodard | |
| 2009/0294248 A1 | 12/2009 | Sudkamp | |
| 2013/0221761 A1 | 8/2013 | Depaso | |
| 2013/0241574 A1 * | 9/2013 | Burke | A22C 29/005 324/633 |
| 2014/0216894 A1 * | 8/2014 | Fourney | G01G 11/003 198/340 |
| 2015/0292935 A1 | 10/2015 | Kleczewski | |
| 2016/0252387 A1 | 9/2016 | Laird et al. | |

FOREIGN PATENT DOCUMENTS

| | | |
|---|---|---|
| JP | 2001-108541 A | 4/2001 |
| JP | 2002-236059 A | 8/2002 |
| WO | 2013-28378 A2 | 2/2013 |
| WO | 2013191217 A1 | 12/2013 |

OTHER PUBLICATIONS

Extended European Search Report of the European Patent Office, European Application No. 15779444, dated Nov. 9, 2017, Munich, Germany.

* cited by examiner

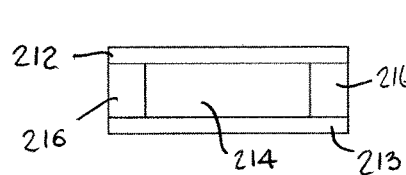
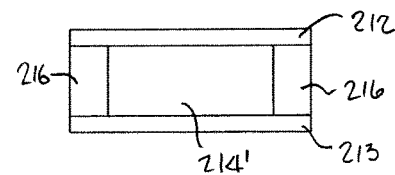
FIG. 17A　　　FIG. 17B
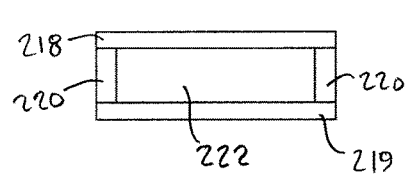
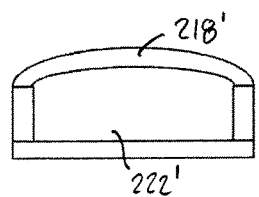
FIG. 18A　　　FIG. 18B
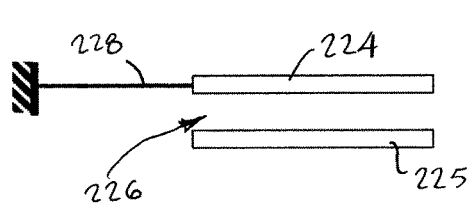
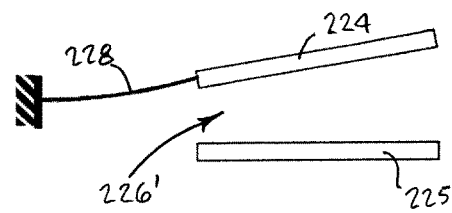
FIG. 19A　　　FIG. 19B
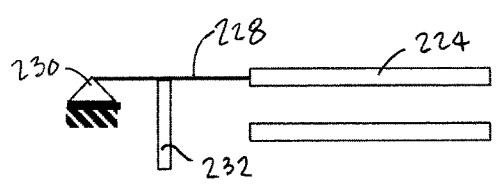
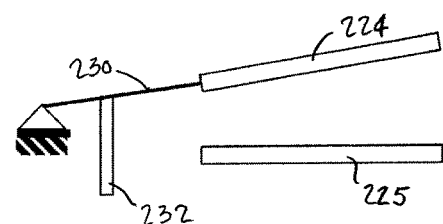
FIG. 20A　　　FIG. 20B

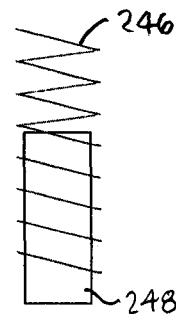
FIG. 24A              FIG. 24B
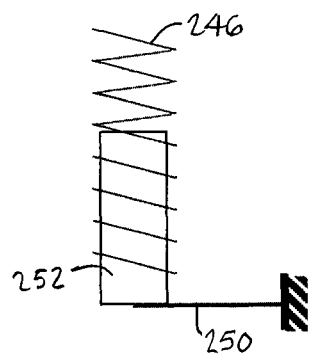
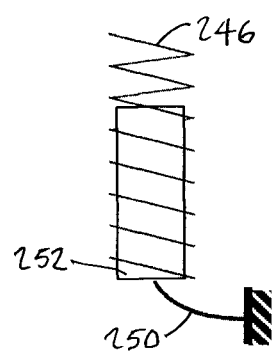
FIG. 25A              FIG. 25B
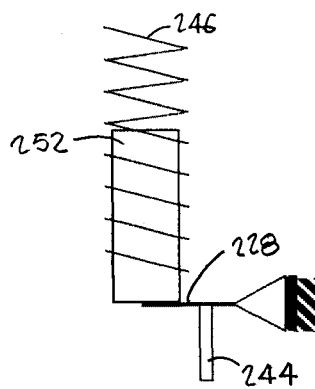
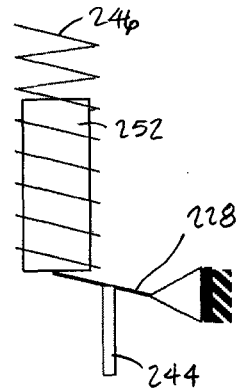
FIG. 26A              FIG. 26B

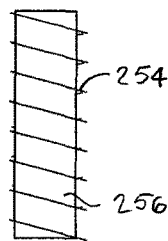 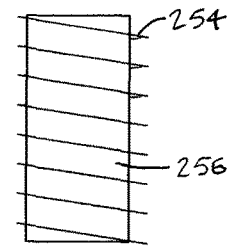
FIG. 27A   FIG. 27B
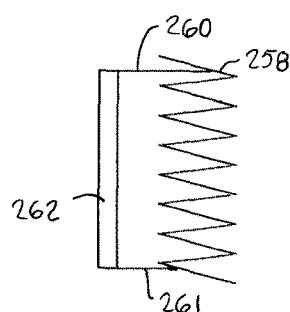 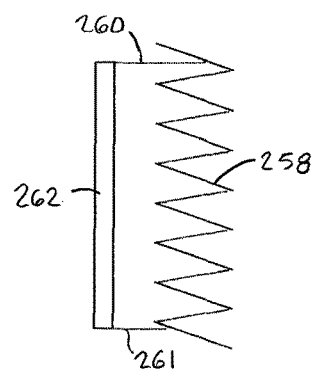
FIG. 28A   FIG. 28B
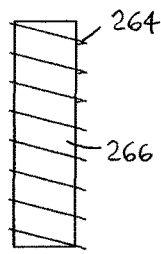 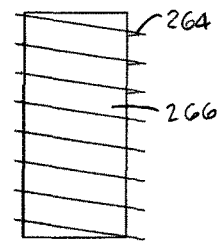
FIG. 29A   FIG. 29B
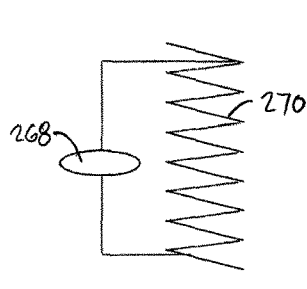 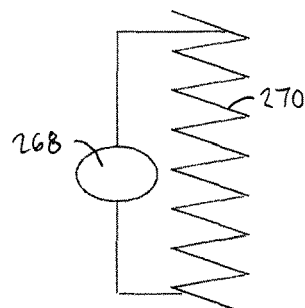
FIG. 30A   FIG. 30B

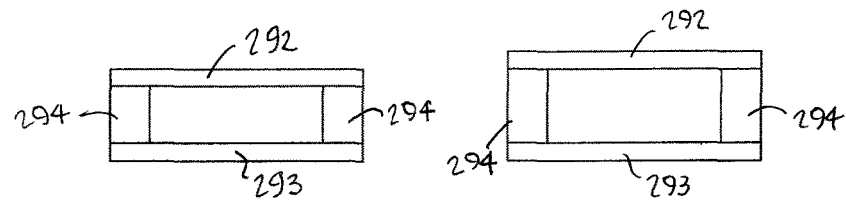
FIG. 34A  FIG. 34B
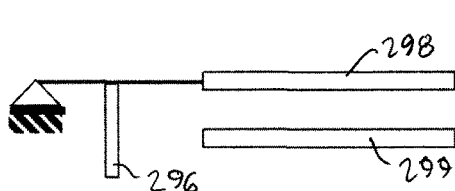 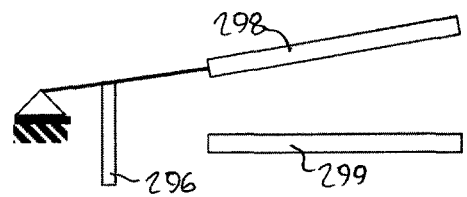
FIG. 35A  FIG. 35B
 
FIG. 36A  FIG. 36B
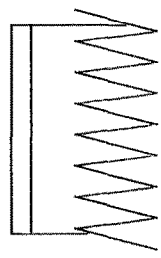 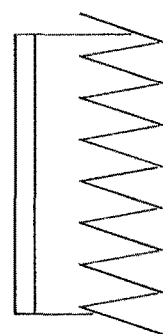
FIG. 37A  FIG. 37B

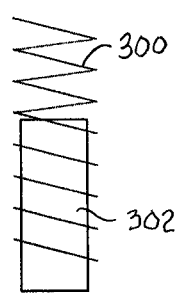 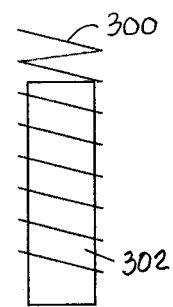
FIG. 38A  FIG. 38B
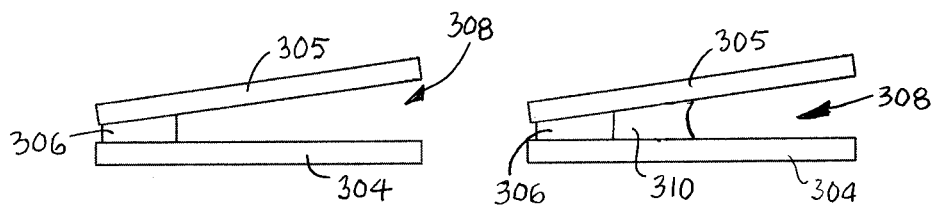
FIG. 39A  FIG. 39B

CONVEYOR-BELT SYSTEM FOR MEASURING CONDITIONS THAT VARY THE RESONANT FREQUENCY OF A RESONANT CIRCUIT

BACKGROUND

The invention relates generally to power-driven conveyors and more particularly to conveyor systems using sensing elements embedded in a conveyor belt to detect conditions affecting the conveyor belt.

Sensors embedded in conveyor belts require power to make sensor measurements and to transmit measurements off the belt. On-belt batteries, storage capacitors, and energy-harvesting devices have been used or proposed for that purpose. But most of these solutions require recharging or replacement, take up space, add weight, or weaken the belt. Rip detectors are used in flat belts to determine if a belt has developed a tear and is in danger of imminent failure. Many rip detectors include thin wire loops embedded in a belt. When an untorn, closed wire loop passes a detector along the conveying path, a detection signal is generated and detected by the detector. When a torn, open wire loop passes, the detection signal differs from that for an untorn loop, indicating a rip in the belt. Although these devices do not require on-belt power sources, they are not designed to make a continuum of sensor measurements. Rather they generate a detection signal that is used for a binary conclusion: torn or not torn.

SUMMARY

One version of a conveyor belt embodying features of the invention comprises a plurality of resonant circuits disposed at sensor positions in a belt body. Each of the resonant circuits includes an inductor and a capacitor connected to the inductor to form the resonant circuit. The resonant frequency of each resonant circuit is determined by the inductance of the inductor and the capacitance of the capacitor. At least one of the inductance of the inductor and the capacitance of the capacitor is varied by a varying condition affecting the conveyor belt.

In another aspect, one version of a conveyor-belt measuring system comprises a conveyor belt and at least one stationary measurement circuit external to the conveyor belt. The conveyor belt includes a plurality of resonant circuits disposed at sensor positions in the conveyor belt. Each of the resonant circuits has a resonant frequency and includes a sensing element sensing a condition affecting the conveyor belt and changing the resonant frequency as a function of the condition affecting the conveyor belt and a coupling element connected to the sensing element. The stationary measurement circuit includes a frequency detector and a stationary coupling element coacting with the coupling elements in the conveyor belt as they pass close to the stationary coupling element to couple the resonant circuits to the frequency detector. The frequency detector measures changes in the resonant frequency of the resonant circuits caused by the condition affecting the conveyor belt.

Another version of a conveyor-belt measuring system comprises a conveyor belt and at least one stationary measurement circuit external to the conveyor belt. The conveyor belt includes a plurality of sensing elements disposed at sensor positions in the conveyor belt. An electrical property of each of the sensing elements is changed by a condition affecting the conveyor belt. The at least one stationary measurement circuit includes a frequency detector and a stationary coupling element that couples the at least one stationary measurement circuit to the plurality of sensing elements in the conveyor belt as they pass closely by. Each of the sensing elements forms part of a resonant circuit having a resonant frequency that depends on the electrical property of sensing element. The frequency detector measures changes in the resonant frequency of the resonant circuit caused by the condition affecting the conveyor belt.

Yet another version of a conveyor-belt measuring system comprises a conveyor belt and at least one stationary measurement circuit external to the conveyor belt. The conveyor belt includes a plurality of deflection sensors disposed at sensor positions in the conveyor belt connected to an associated coupler. Each of the deflection sensors senses deflection of the conveyor belt. Each stationary measurement circuit includes a stationary coupler coupling the stationary measurement circuit to the plurality of deflection sensors in the conveyor belt without contact as the associated couplers in the conveyor belt pass close to the stationary coupler The stationary measurement circuit measures the deflection of the conveyor belt sensed by each of the deflection sensors.

BRIEF DESCRIPTION OF THE DRAWINGS

FIGS. 17A-17B, 18A-18B, 19A-19B, and 20A-20B are side views of capacitive temperature-sensing elements whose plate separation changes with temperature;

FIGS. 24A-24B, 25A-25B, and 26A-26B are side views of inductive temperature-sensing elements whose core changes with temperature;

FIGS. 27A-27B and 28A-28B are side views of inductive temperature-sensing elements whose coil dimensions change with temperature;

FIGS. 29A-29B and 30A-30B are side views of inductive pressure-sensing elements whose coil dimensions change with pressure;

FIGS. 34A-34B and 35A-35B are side views of capacitive sensing elements whose plate separation changes with humidity or spillage;

FIGS. 36A-36B, 37A-37B, 38A-38B are side views of inductive sensing elements whose coil or core dimensions change with humidity or spillage; and FIGS. 39A-39B are side views of a capacitive sensing circuit whose permittivity is changed by spillage.

DETAILED DESCRIPTION

Figure 1:
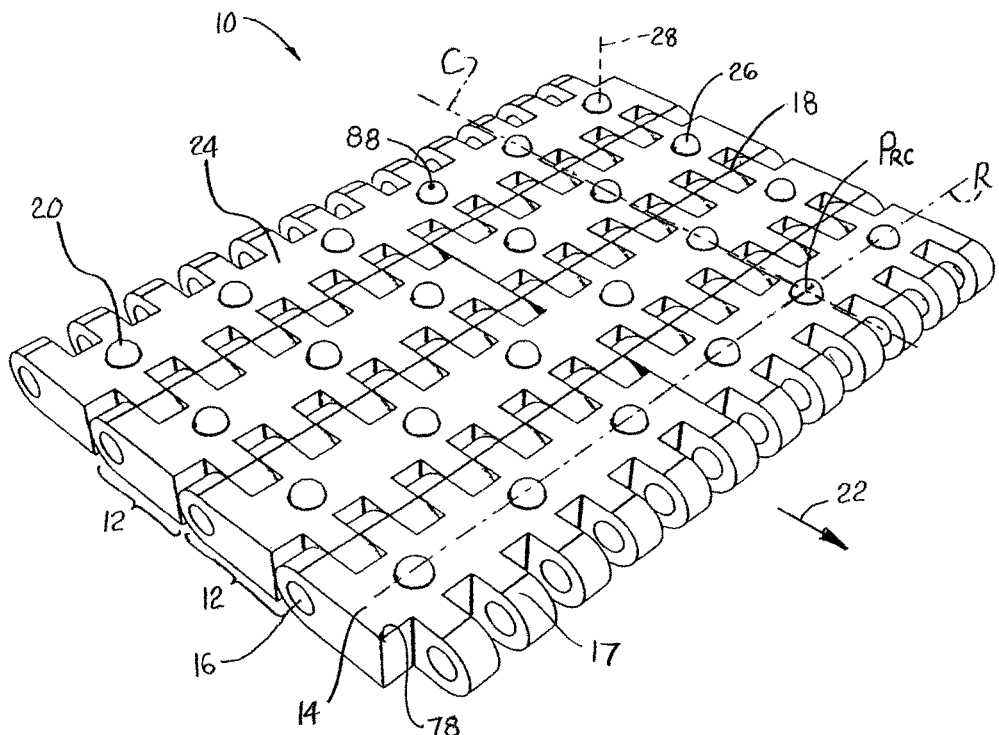
FIG. 1 is a perspective view of a portion of a conveyor belt embodying features of the invention.

A portion of one version of a conveyor belt embodying features of the invention is shown in FIG. 1. The conveyor belt 10 is a modular plastic conveyor belt constructed of a series of rows 12 of one or more plastic belt modules 14 hingedly connected end to end by hinge rods 16 or pins in interleaved hinge elements 17 forming hinge joints 18 between consecutive rows. The belt modules 14 are conventionally injection-molded out of a thermoplastic polymer, such as polypropylene, polyethylene, acetal, or a composite polymer. Sensing elements, such as force-sensitive elements 20, are embedded in the conveyor belt 10 at individual positions. In this version, the force-sensitive elements are arranged in a two-dimensional array of rows R across the width of each belt row 12 and columns C along the length of the belt in a conveying direction 22. In this way the position of any individual force-sensitive element 20 can be defined as $P_{RC}$, where R represents the row (or belt row if each belt row has only one row of force-sensitive element) and C represents the column from one side of the belt to the other. The density of the array or the separation between rows and columns of force-sensitive elements for a given belt may be determined with a priori knowledge of the sizes and shapes of the conveyed articles. In this version each force-sensitive element 20 is mounted at the outer conveying surface 24 of the belt 10. The force-sensitive elements may be protected by a cover 26 that may be domed to form a salient protrusion slightly above the belt's conveying surface 24 so that the entire weight of a conveyed article is borne by a group of the covers. The force-sensitive elements have sensing axes 28 that are perpendicular, or normal, to the conveying surface 24 to measure forces applied normal to the conveying surface at the positions of the force-sensitive elements on the belt.

Figure 2:
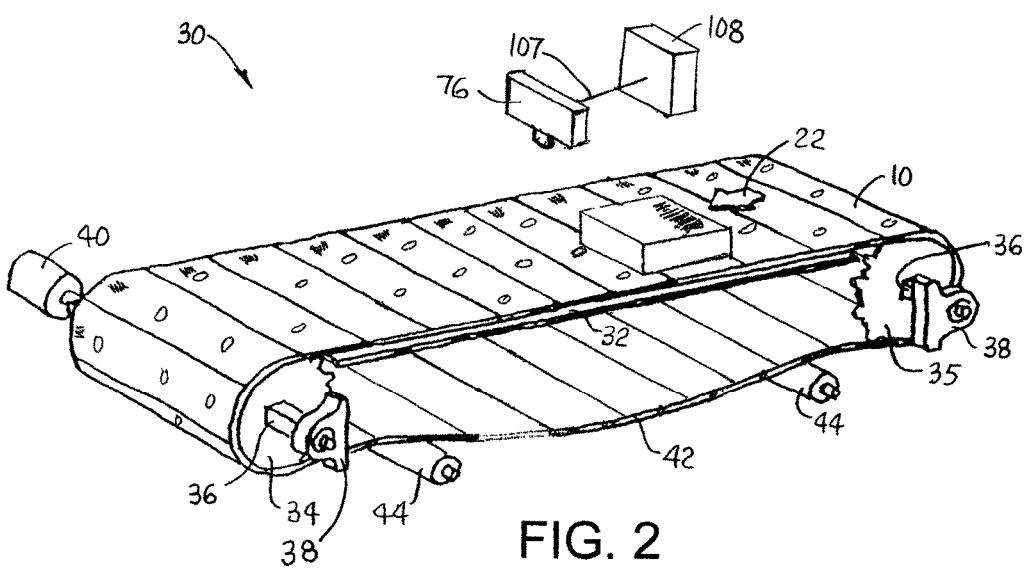
FIG. 2 is an isometric view of a conveyor system using a conveyor belt as in FIG. 1.

The conveyor belt 10 is shown in a weighing system 30 in FIG. 2. The conveyor belt advances in the conveying direction 22 along an upper carryway 32. The endless belt is trained around drive and idle sprocket sets 34, 35 mounted on shafts 36, whose ends are supported in bearing blocks 38. A drive motor 40 coupled to the drive shaft rotates the drive sprockets 34, which engage the underside of the belt and drive the belt in the conveying direction 22 along the upper carryway 32. The belt returns along a lower returnway 42. Rollers 44 support the belt in the returnway and reduce the maximum catenary sag.

Figure 3:
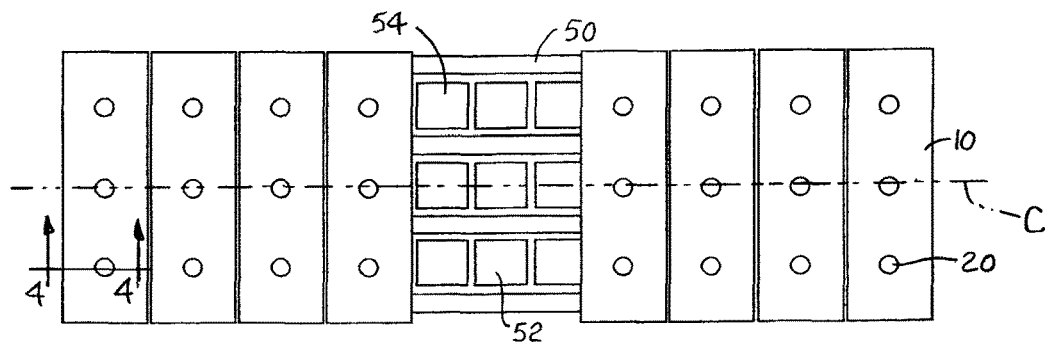
FIG. 3 is a top plan view of a portion of the conveyor system of FIG. 2 partly cut away.

As shown in FIG. 3, the conveyor belt 10 is supported along the carryway atop wearstrips 50. Activation circuits 52 for the force-sensitive elements 20 are housed in housings 54 whose top surface is at or slightly below the level of the tops of the wearstrips 50. The activation circuits 52 are arranged in columns aligned with columns C of the force-sensitive elements 20 in the conveyor belt 10.

Figure 4:
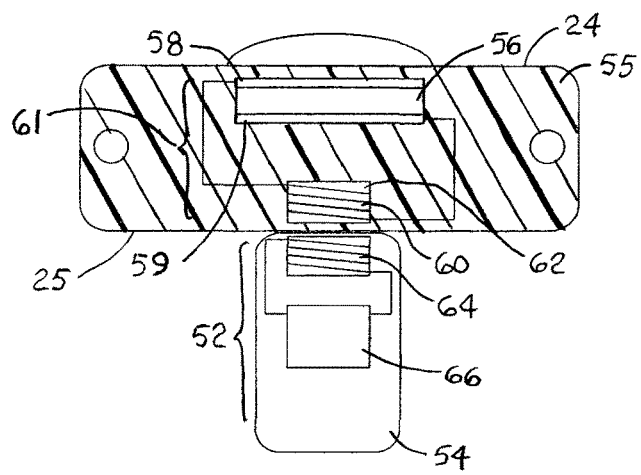
FIG. 4 is a cross section of the conveyor system of FIG. 3 taken along lines 4-4 and showing a capacitive force-sensitive element.

A cross section of one belt row is shown in FIG. 4. Embedded in the plastic belt module 55 is a capacitor 56 having an upper plate 58 and a lower plate 59. The two plates are shown parallel to each other and to the top conveying surface 24 of the belt in the absence of articles atop the belt. The plates are electrically wired to opposite ends of a coupler, or coupling element, an inductive coil 60 wrapped around a bobbin 62 near the bottom side 25 of the belt. The capacitor is electrically connected across the inductive coil 60 to form a passive, high-Q resonant circuit 61. The external activation circuit 52 includes an oscillator and an activation, or coupling, coil 64 that coacts with the belt coil 60 passing by. In the vicinity of the closest point of approach, the two coils are positioned close enough across a gap for the activation coil to couple inductively to the passive resonant circuit in the belt wirelessly without physical contact. The activation coil 60 is connected to support electronics 66 in the housing 54.

Figure 5:
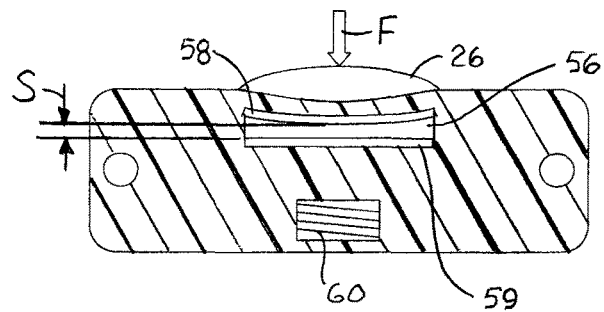
FIG. 5 is a view of the belt portion of FIG. 4 shown with a downward force applied to deform the capacitor.

As shown in FIG. 5, a downward force F, such as produced by the weight of a conveyed article sitting atop the cover 26, causes the upper plate 58 of the capacitor 56 to deflect or move downward. The reduction in the separation S between the deflected upper plate 58 and the rigid, fixed lower plate 59 causes the capacitance to proportionally increase because capacitance is inversely proportional to the distance between the plates. And because the movement of the upper plate is proportional to the applied force F, the capacitance is proportional to the force applied to the cover 26 by a supported article. Thus, the capacitor 56 is a force-sensitive, or deflection-sensitive, element in the example of FIG. 5. Any change in capacitance causes a change in the resonant frequency of the passive L-C circuit formed by the inductive coil 60 and the capacitor 56. Together, the resonant circuit 61 in the belt and the oscillator in the external circuit 66 form a distributed sensor—in this case, equivalent to a load cell or a deflection sensor—with a sensing-circuit portion in the belt and a measuring-circuit portion external to the belt.

Figure 9A:
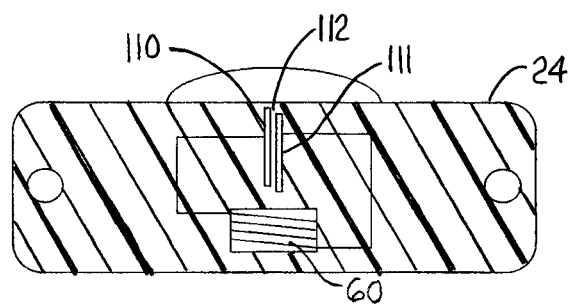
FIGS. 9A and 9B are cross sections of a belt portion in a conveyor system as in FIG. 3 showing another version of a capacitive force-sensitive element in the absence and in the presence of a downward-acting force on the belt.
Figure 9B:
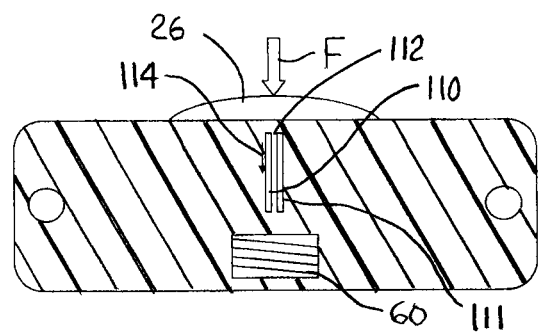

Another version of a force-sensitive capacitor is shown in FIGS. 9A and 9B. In this version the plates 110, 111 of the capacitor 112, i.e., the planes defined by the plates, are generally perpendicular to the top surface 24 of the conveyor belt. The first plate 110 is vertically movable, while the second plate 111 is rigidly fixed in place. When no downward force acts on the protrusion 26, the two plates 110, 111 are vertically offset from one another as shown in FIG. 9A. When a downward force F is applied by the weight of a conveyed article, as in FIG. 9B, the movable plate 110 moves downward 114 increasing the area between the two plates and proportionally increasing the capacitance and reducing the resonant frequency of the L-C circuit. Of course, the two plates could alternatively be positioned in parallel with no vertical offset in the absence of a force. In such a design, a downward force would push one plate downward relative to the other to increase the offset, decrease the area between the plates, decrease the capacitance, and increase the resonant frequency of the L-C circuit.

Like the capacitor 56 in FIG. 4, the capacitor 112 of FIGS. 9A and 9B is connected across the inductive coil 60.

Figure 10A:
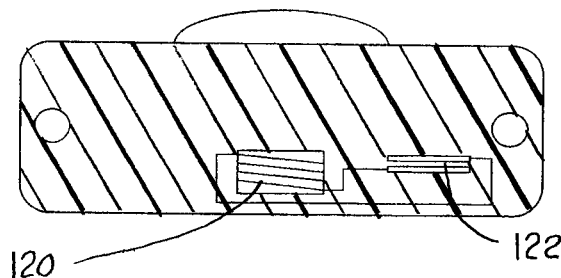
FIGS. 10A and 10B are cross sections of a belt portion in a conveyor system as in FIG. 3 showing an inductive force-sensitive coil in the absence and in the presence of a downward-acting force on the belt.
Figure 10B:
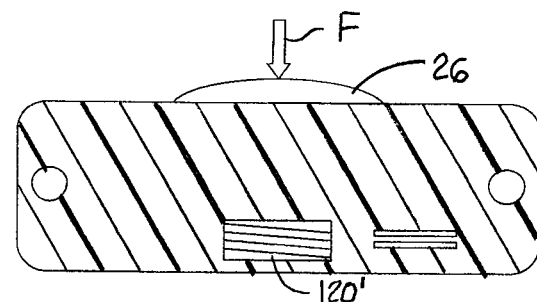

FIGS. 10A and 10B show another version of a force-sensitive resonant circuit. In this version, an inductive coil is the force-sensitive element. The coil 120 is electrically connected to a fixed-capacitance capacitor 122 to form a passive resonant L-C circuit. When a downward force F is applied to the protrusion 26, the coil 120' is compressed like a spring, as shown in FIG. 10B. The decreased length of the coil increases the inductance of the coil 120' and reduces the resonant frequency of the L-C circuit. A downward force increasing the cross section of the coil would also increase the inductance of the coil 120. In fact, other force-induced changes in the geometric shape of the coil can affect its inductance and the resonant frequency of the passive L-C circuit.

Figure 11:
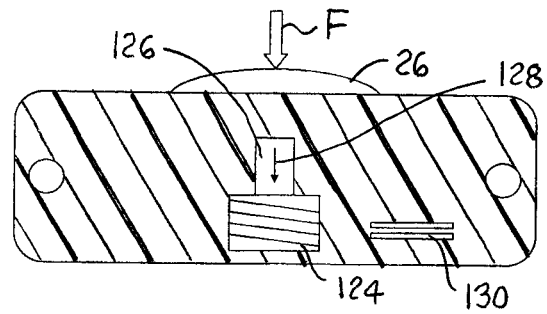
FIG. 11 is a cross section as in FIG. 10B in which the core of the coil changes the inductance of the coil when a downward-acting force acts on the belt.

FIG. 11 shows an alternative force-sensitive coil 124. The coil's geometry is fixed, but a downward force F on the protrusion 26 pushes a metallic core 126 with a high permeability downward deeper into the coil 124. The increased penetration depth of the core increases the permeability and the inductance of the coil 124 and decreases the resonant frequency of the L-C circuit formed by the coil and a fixed capacitor 130. Alternatively, the inductance can be increased by moving a conductive ring closer to or encircling more windings of the coil or by moving a conductive plate closer to the coil, or both. Of course, the core, plate, or ring could be arranged relative to the coil to decrease the inductance and increase the resonant frequency under the influence of a force on the conveyor belt that decreases the penetration of the core or increases the distance of the plate or ring from the coil.

Figure 6:
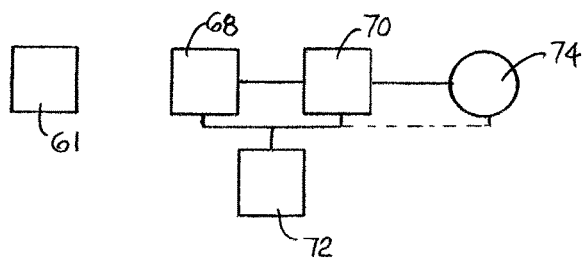
FIG. 6 is a block diagram of a distributed sensor usable in the conveyor system of FIG. 2.

A block diagram of one sensor, or load cell, of a weighing system is shown in FIG. 6. The load cell includes the passive resonant circuit 61 in the belt forming the sensing circuit and an oscillator 68, including the activation coil, in the external housing. The sensing circuit in the conveyor belt may be made of discrete electrical components embedded in the belt, or it may be made smaller using microelectromechanical-systems (MEMS) technology. The oscillator is set to oscillate at a frequency that is close to the resonant frequency of the resonant circuit 61 in the belt. When the resonant circuit is near the activation coil, the coil, acting as an antenna, inductively couples the resonant circuit 61 to the oscillator 68. The interaction of the resonant circuit 61 with the oscillator 68 changes the oscillator frequency in accordance with the capacitance change in the resonant circuit. The frequency of the oscillator 68 is measured by a frequency detector 70. The oscillator and the frequency detector 70, which form the measuring circuit of the distributed load cell, are powered by a power supply 72. The change in frequency of the oscillator is proportional to the downward force on the capacitor 56. The frequency detector's output is converted into a weight and recorded locally or remotely in a data recorder 74.

Figure 7:
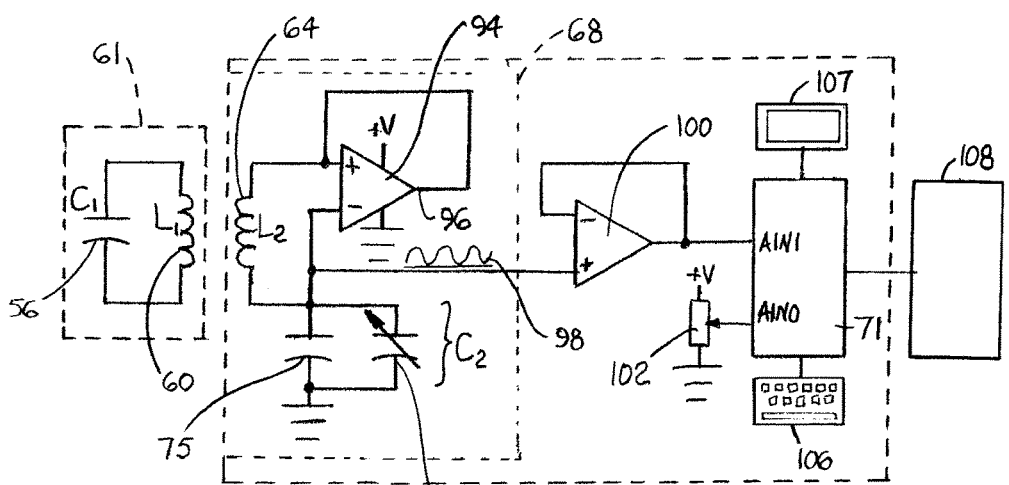
FIG. 7 is an electrical schematic/block diagram of a sensor as in FIG. 6.

A more detailed circuit diagram is shown in FIG. 7. The passive resonant circuit 61 includes the capacitor 56, whose capacitance changes with an applied force, and the coil 60. The coil 60 is an inductor with inductance Li, and the capacitor 56 has a capacitance $C_1$ that is a function of the applied force. The coil also has a small series resistance. No power source is needed in the belt. The resonant frequency (in Hertz) is given by $f_r=1/[2\pi(L_1C_1)^{1/2}]$. The external oscillator 68 includes the activation coil 64 with inductance $L_2$ and a small resistance not depicted in FIG. 7. A capacitor 75 having a fixed capacitance in parallel with a trim capacitor 77 having a manually variable capacitance is connected between one end of the activating coil 64 and ground. The combined capacitance of the fixed and variable capacitors 75, 77 is $C_2$. The other end of the coil 64 is connected to the non-inverting input (+) of an operational amplifier (op amp) 94. The junction of the coil 64 and the capacitors 76, 78 is connected to the inverting input (−) of the op amp 94. Positive feedback is applied by connecting the output 96 of the op amp 94 to its non-inverting input (+) to maintain oscillation at the nominal oscillator frequency given by $f_n=1/[2\pi(L_2C_2)^{1/2}]$. The trim capacitor 77 is adjusted to set the nominal oscillator frequency, i.e., the frequency of the oscillator when uncoupled from the resonant circuit 61 in the belt, to a value close to the resonant frequency $f_r$ of the resonant circuit 61.

The op amp 94 is operated single-ended with its upper voltage rail at a positive voltage V (e.g., +5 Vdc) and its lower voltage rail at ground. The positively biased sinusoidal waveform 98 produced by the oscillator 68 is buffered in an emitter-follower op amp 100 circuit serving as a buffer amplifier with high input impedance so as not to load the oscillator circuit. The buffered oscillator signal is applied to the frequency detector. The frequency detector may be realized with analog and digital logic circuits or with a microcontroller.

In the example shown in FIG. 7, the frequency detector is realized with a microcontroller 71. The buffered oscillator waveform is applied to the negative input AIN1 of the microcontroller's analog comparator. The positive input AIN0 is connected to the wiper arm of a potentimeter 102 forming an adjustable voltage divider with the supply voltage V. Whenever the amplitude of the oscillator waveform at the negative comparator input AIN1 crosses the threshold voltage at the positive comparator input AIN0 set by the potentiometer, an interrupt is generated in the microcontroller. The interrupt is serviced by a firmware routine that increments a counter counting the number of cycles of the oscillator waveform. The total cycle count in a predetermined time interval is proportional to the oscillator frequency. The cycle count is reset to zero at the start of the next interval. Thus, the frequency detector is realized as a frequency counter in this example. But other methods of detecting the frequency could be used. For example, the microcontroller could be a digital-signal-processing (DSP) device capable of performing Fast Fourier Transform (FFT) or Fast Hartley Transform (FHT) algorithms on the oscillator waveform to extract its frequency. In that case, the frequency detector is realized as a spectrum analyzer.

When the resonant circuit 61 in the belt is far from the oscillator 68, the oscillator's nominal frequency $f_n$ is unaffected by the resonant circuit. As the belt advances and the resonant circuit 61 comes in close proximity to the oscillator 68, the interaction between the two circuits increases. The oscillator's frequency changes from its nominal frequency $f_n$. The frequency detector detects that change in frequency. When the frequency detector is implemented as a frequency counter in a microcontroller as previously described, the cycle count in the predetermined interval is a measure of the force acting on the capacitor 56 in the belt. Because the frequency change is also a function of the proximity of the belt coil 60 to the oscillator coil 64, a microcontroller routine reports the maximum change in frequency from nominal as the best measure of the force applied to the belt capacitor 56. The microcontroller converts the cycle count to a weight value. The microcontroller 71 may be connected to a user interface including an output display 104 and a manual input device, such as a keyboard 106. The microcontroller 71, along with the microcontrollers in the other activation units, is also connected directly or wirelessly to a main controller 108.

Figure 8:
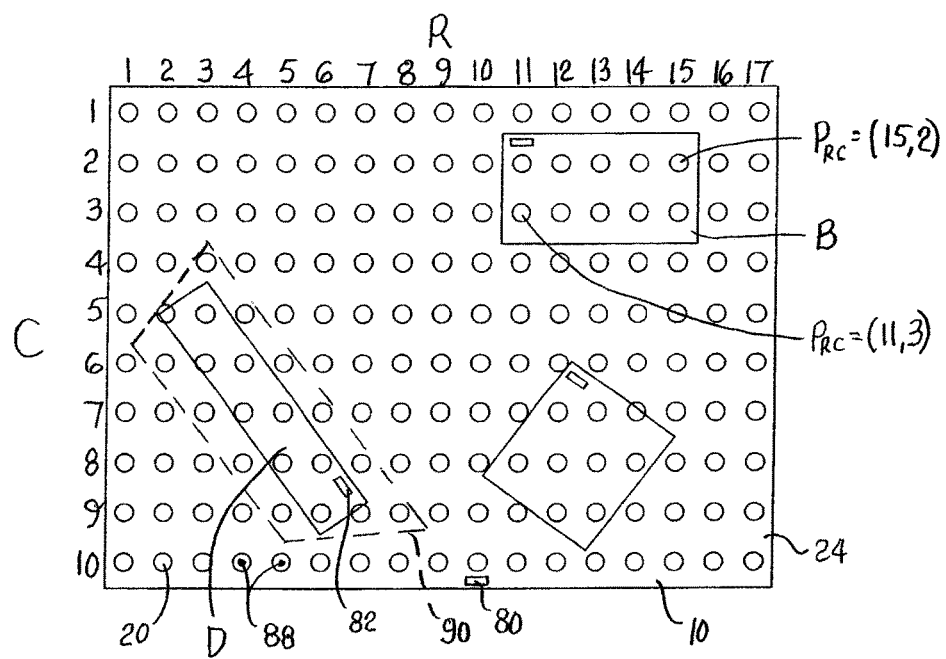
FIG. 8 is a top schematic of the conveyor system of FIG. 2.

A vision system as in FIG. 1 includes a camera 76 or other optical detector supported above the carryway 32 to vision a portion of the conveying surface. Optical signals 107 from the camera are sent to a main controller 108. The main controller executes a pattern-recognition process to determine the footprints of individual articles conveyed on the belt from the optical signals. With a priori knowledge of the load-cell-array geometry relative to a point on the belt, such as a belt-module corner 78, the vision system can determine relatively a group of load cells under an individual article's footprint. For example, in the portion of the conveying surface 24 as shown in FIG. 8, article B overlies ten load cells covering two columns C and five rows R. Optically detectable markers 80 on some or all belt rows, for example, may be used by the vision system to identify absolutely which ten sensing elements are covered by article B. In this example, the vision system reads the marker, which may be coded or may simply be the number 10 indicating that it is on row 10 of the belt. With the a priori knowledge of the array geometry and the footprint of article B with respect to row 10, the vision system can identify the ten sensing elements underlying the article. The vision system can then execute a weighing process that combines the measurements of the force-sensing elements at absolute positions $P_{RC}=\{(R, C)\}=\{(11, 2); (11, 3); (12, 2); (12, 3); (13, 2); (13, 3); (14, 2); (14, 3); (15, 2); (15, 3)\}$ to compute the weight of article B. The load-cell measurements may be combined, for example, by summing the individual load-cell measurements to compute a value equal or proportional to the weight of the underlying article. Each of the articles is marked with identifying indicia 82, such as a bar code, that a reader in the vision system can interpret. In that way, the computed weight can be associated with a specific individual article. And, because the vision system visions the entire width of the belt, articles do not have to be arranged in a single file over a static weighing station in the carryway. Furthermore, the resonant-circuit array in the belt allows the weight to be measured without stopping the belt. A video display of the vision system may be used to monitor system operating conditions and settings or the weights of individual articles. The controller 108 may be a programmable logic controller, a laptop, a desktop, or any appropriate computer device capable of executing the processes described.

The vision system could use other means to assign weights to individual articles. For example, the positions of each of the sensing elements, or load cells, could be marked on the conveying surface 24 or the load-cell covers 26. The mark could identify each load cell explicitly or could just be a generic position mark, such as a dot 88 (FIG. 1) on each or a predetermined subset of the sensing circuits. If all the sensing-element positions are marked, the vision system would not need a priori knowledge of the array layout. As another example the vision system could alternatively select all those sensing elements in an enlarged region 90 (FIG. 8) about the article footprint and sum their measurements. The load cells not under the article D would yield measurement values of zero, which would not add to the weight. This ensures that the entire article is weighed accurately. If, of course, another article is close by, the enlarged region has to be carefully selected so as not to encompass the nearby article.

If the articles are separated enough so that no two articles are atop the same or adjacent load cells, the weight of each article can be determined by summing the load-cell measurements of contiguous, non-zero-reading load cells.

The load-cell sensors can also be used to determine the center of gravity (COG) of a conveyed article from the force measurements of each of the contiguous, non-zero-reading load cells and a priori knowledge of each load cell's relative position via conventional COG formulas. And, more simply, the load cells can be used as position sensors to determine the positions of articles on the belt for improved tracking of diverted articles or to detect article skew on the belt from the pattern of contiguous non-zero-reading load cells under a conveyed article.

To minimize variations in the outputs of the sensors and improve their accuracy, the sensors can be calibrated. The calibration can be manual or automatic. In manual calibration, the responses of each of the sensors to known conditions can be used to determine calibration values (e.g., gains and offsets) that can be stored in memory accessible by the main controller or by each sensor's microcontroller. The calibration values are used to correct the measurements. In automatic calibration the sensors can be calibrated periodically while the conveyor belt is running. Each of the sensors is subjected to known conditions. The calibration can start at a known point in the belt by using a known belt length to ensure that all the sensors are calibrated. A reference at a known position in the belt relative to the sensors can be sensed and used to start and stop calibration. By measuring the responses of the sensors over several belt circuits, a signature map of the sensors can be developed. The signature map is used to assign the calibration values to the corresponding sensors.

Figure 12:
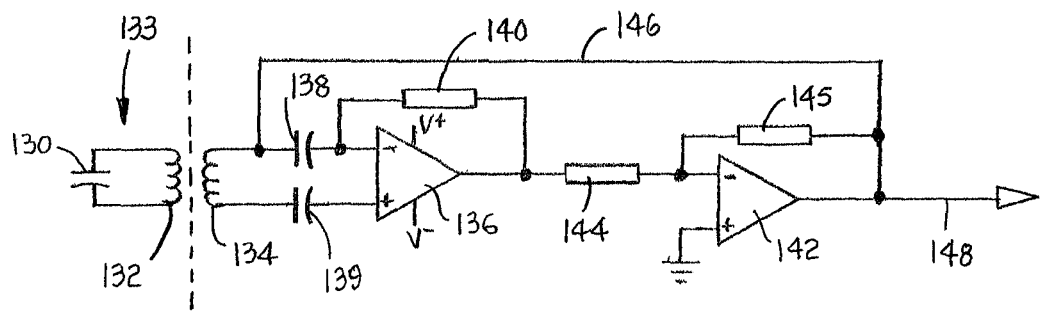
FIG. 12 is an electrical schematic of an alternative inductively coupled differentiating-amplifier circuit usable in a sensor system as in FIG. 6.

FIG. 12 shows an alternative inductively coupled resonant circuit for measuring the change in the resonant frequency of an L-C circuit caused by a change in the capacitance of a sensing capacitor 130. The sensing capacitor 130 and an inductive coupling coil 132 in the belt form a resonant L-C circuit 133. The external stationary activation and measuring electronic circuit in the conveyor frame has a coil 134 inductively coupled to the coil 132 of the L-C circuit. A first op amp 136 is configured as a differentiating amplifier with capacitors 138, 139 between the inductive coil 134 and the op amp's inverting (−) and non-inverting (+) inputs and a feedback resistor 140. A second op amp 142 with its resistors 144, 145 forms an inverting amplifier, whose output is directed back to the coil 134 by activation line 146 to activate the L-C circuit 133 in the belt. The output 148 of the second op amp 142 is connected to a frequency detector, such as the frequency counter 71 shown in FIG. 7, after any signal conditioning required to limit the maximum and minimum voltage levels of the output signal to a range appropriate for the frequency counter's input. Unlike the measuring system of FIG. 7, this measuring system measures the resonant frequency of the L-C circuit directly rather than the frequency of a separate oscillator whose frequency is changed from its nominal resonant frequency by interaction with a passive-LC circuit passing closely by.

Figure 13:
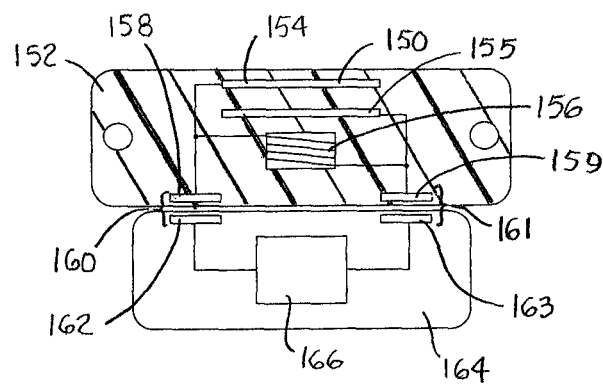
FIG. 13 is a cross section as in FIG. 4 showing an alternative sensor arrangement with capacitive coupling.
Figure 14:
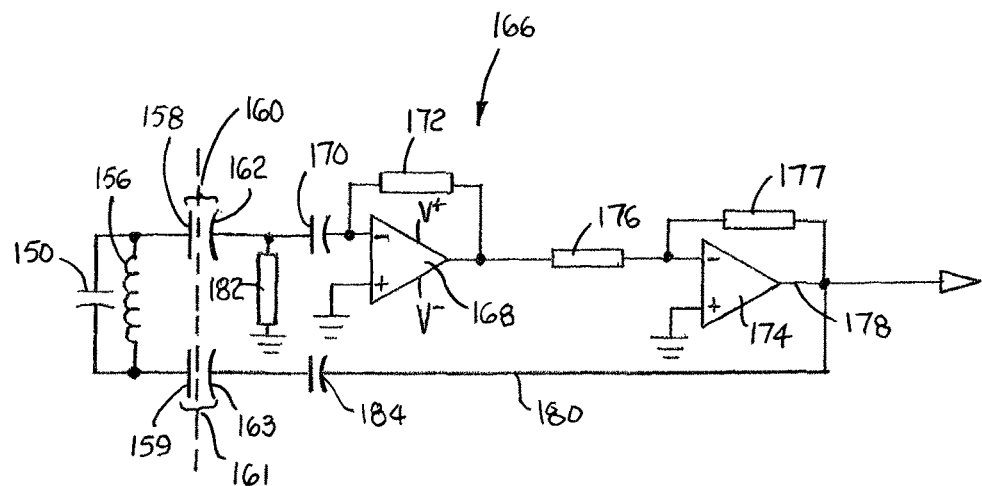
FIG. 14 is an electrical schematic of one version of sensor circuitry usable with an arrangement as in FIG. 13.

A capacitively coupled resonant circuit is shown in FIG. 13. A capacitive sensor 150 is mounted in a conveyor belt 152. The capacitance of the sensor 150 changes as a function of some condition experienced by the belt. The plates 154, 155 of the capacitive sensing element 150 are connected to opposite terminals of an inductive coil 156 to form a resonant L-C circuit. The plates 154, 155 are also connected to coupling elements, in the form of plates 158, 159, near the bottom of the belt 152. The belt's coupling plates 158, 159 form coupling capacitors 160, 161 with corresponding stationary plates 162, 163 mounted in the conveyor frame 164 external to the belt 152. The stationary plates 162, 163 are connected to a stationary resonator-activation-and-measuring circuit 166, as also shown schematically in FIG. 14. A first op amp 168 is configured as a differentiating amplifier by an input capacitor 170 and a negative-feedback resistor 172. A second op amp 174 is configured as an inverting amplifier with resistors 176, 177. The inverter's output 178 is connected to a frequency detector (not shown). The inverter inverts the signal out of the differentiating amplifier so that its output 178 is in-phase with the oscillations of the L-C circuit. The output 178 is fed back to the L-C circuit over a feedback path 180 via stationary plate 163. A grounded resistor 182 connected to the other stationary plate 162 allows for draining and charging of the differentiating capacitor 170 so that a measurable signal is presented to the op amp 168. To reduce the effect of stray capacitance on the measuring circuit, the capacitance of the coupling capacitors 160, 161 should be much greater than the stray capacitance. But if that results in physically large and impractical capacitors, a compensation capacitor 184 may be inserted in the feedback path 180 to minimize measurement noise caused by changes in the capacitance of the coupling capacitors 160, 161. The compensation capacitor 184 preferably has a small capacitance and is located close to the plate 163 to reduce the effect of stray capacitance on the measurement.

Figure 15:
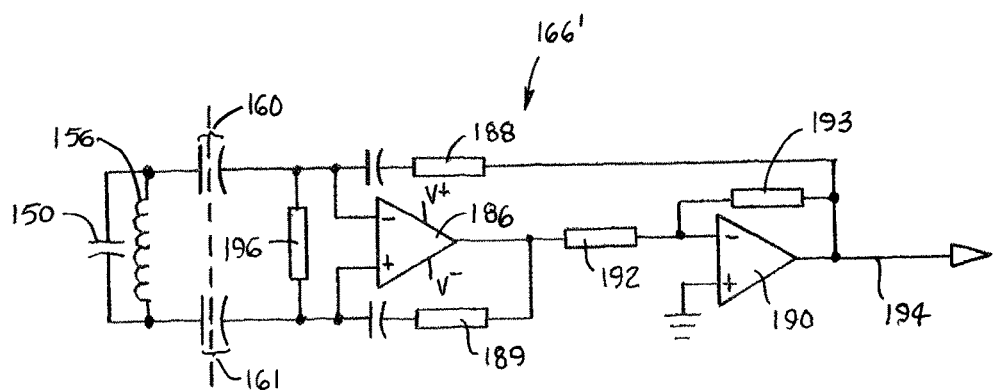
FIG. 15 is an electrical schematic of an alternative version of the sensor circuitry of FIG. 14.

Another capacitively coupled circuit 166' is shown in FIG. 15. In this circuit a first op amp 186 is configured as a differential comparator with the input coupling capacitors 160, 161 and feedback resistors 188, 189. A second op amp 190 is configured as an inverting amplifier with its resistors 192, 193 setting the gain. The inverter aligns the phase of the output 194 with the L-C oscillation. The output is fed back to the comparator through the feedback resistor 188 and is sent to the frequency detector (not shown). A resistor 196 connected between the inverting (−) and non-inverting (+) inputs of the first op amp 186 prevents the inputs from floating.

Figure 16:
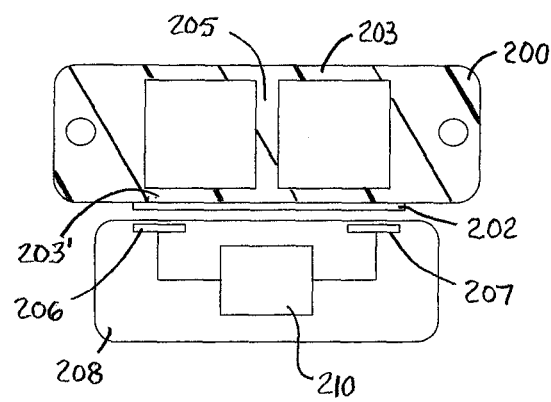
FIG. 16 is a cross section as in FIG. 13 of another version of a sensor arrangement with capacitive coupling.

FIG. 16 shows a capacitively coupled sensor arrangement in which a conveyor belt 200 has a metal plate 202 at the belt's bottom 204. The plate 202 is spring-loaded, in this example, between leaf springs 203, 203' connected by a beam 205, such that a weight applied to the plate deflects the springs and moves the plate vertically downward. Stationary plates 206, 207 in the conveyor frame 208 form two variable-capacitance half-capacitors with the metal plate 202. The plates 206, 207 are connected to an inductor in an activation-measurement circuit 210 in the conveyor frame. The two capacitors connected in series and the inductor form an L-C resonator. The resonant frequency changes with the vertical position of the elongated plate 202, which affects the capacitors' plate separation. Because, for practical sizes of coupling capacitors, the coupling range of capacitors is less than that of practical-sized coupling inductors, capacitive coupling can provide a more precise estimate of the position of a passing sensing element. So, in this example, the sensing element formed by the spring-loaded plate 202 also served as the coupling element coupling the plate 202 to the external measurement circuit 210 via the stationary plates 206, 207. And the L-C resonant circuit is distributed between the sensing element 202 in the conveyor belt 200 and the external stationary measurement circuit 210.

In all the examples already described, the resonant frequency of an L-C circuit was changed by a force acting on a capacitor or an inductor. In particular, the examples were described as force-sensitive or deflection-sensitive elements whose electrical property, capacitance or inductance, is changed by the deflection of a conveyor belt caused by the weight of a conveyed article atop the belt. But it is possible to use similar resonant circuits to measure quantities other than product weight. In the examples that follow, variable capacitors used as sensing elements are connected to fixed-value inductors (not shown) to provide resonant L-C circuits, and variable inductors used as sensing elements are connected to fixed-value capacitors (not shown) to provide resonant L-C circuits.

FIGS. 17A-23B show a variety of variable capacitors used as sensing elements in a conveyor belt to sense temperature. FIG. 17A shows a capacitive sensor constructed of two parallel plates 212, 213 spaced apart across a gap 214 by spacers 216 made of a material with a high coefficient of thermal expansion. When the temperature rises, as in FIG. 17B, the spacers 216 expand and increase the gap 214'. The capacitance is reduced, which changes the resonant frequency of the L-C circuit in which the plates 212, 213 are connected.

Another capacitive temperature sensor is shown in FIGS. 18A and 18B. The sensor comprises two plates 218, 219 separated by spacers 220 across a gap 222 filled with a gas. The top plate 218 is flexible so that, as the temperature rises or falls, the top plate can expand outward or sink inward as the gas pressure increases or decreases. The outward expansion of the flexible top plate 218 with a rise in temperature is shown in FIG. 18B. The increased gap 222' causes the capacitance to decrease, which increases the resonant frequency.

FIG. 19A shows another temperature-sensitive capacitive sensor constructed of two plates 224, 225 separated by a gap 226. The upper plate 224 is connected at the edge to one end of a bimetallic strip 228 pinned at the opposite end to structure in the belt. When the temperature increases, as in FIG. 19B, the bimetallic strip 228 bends, moving the upper plate 224 away from the lower plate 225 and increasing the gap 226'. The larger gap decreases the capacitance, which increases the resonant frequency. The sensor in FIG. 20A works in a similar way, except that one edge of the upper plate 224 is connected to one end of an arm 228 attached to a pivot 230 at the other end. A pusher 232 contacts the arm 228 at a position along the arm's length between the pivot 230 and the plate 224. The pusher 232 is made of a material with a high coefficient of thermal expansion. When the temperature rises, as in FIG. 20B, the pusher elongates and tilts the arm 230 and the upper plate 224 so that the gap between the plates 224, 225 increases, lowering the capacitance.

Figure 21A:
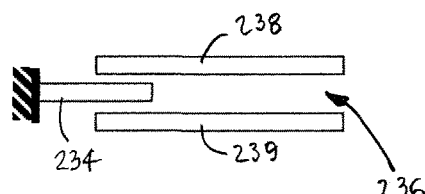
FIGS. 21A-21B, 22A-22B, and 23A-23B are side views of capacitive temperature-sensing elements whose dielectric changes with temperature.
Figure 21B:
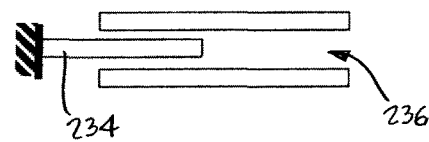
Figures 22A, 22B:
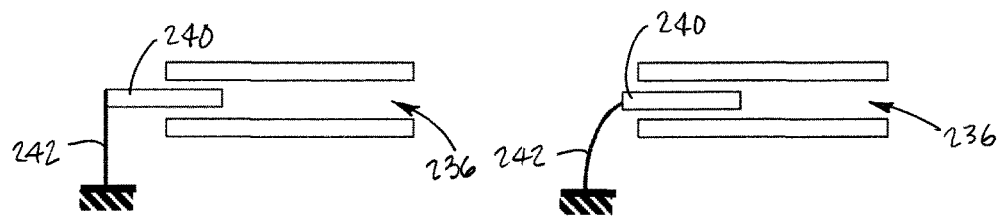
Figure 23A:
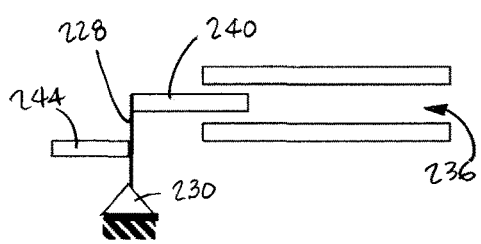
Figure 23B:
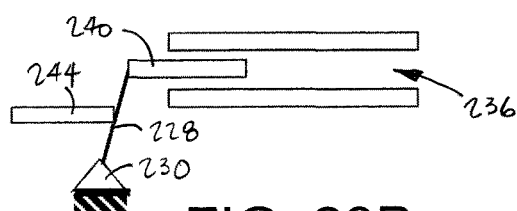
Figure 31A:
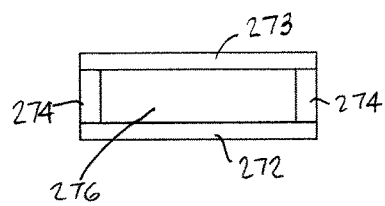
FIGS. 31A-31B, 32A-32B, and 33A-33B are side views of capacitive pressure-sensing elements whose plate separation changes with pressure.
Figure 31B:
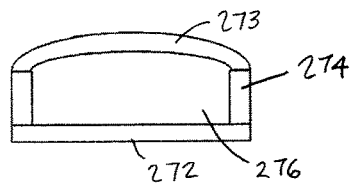
Figure 32A:
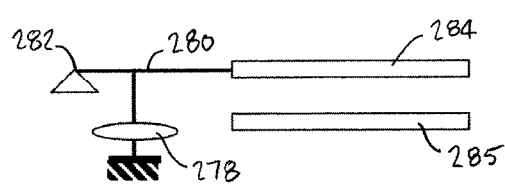
Figure 32B:
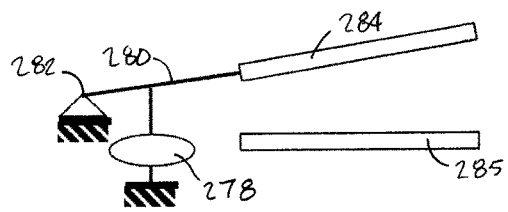

FIGS. 21A-23B show other versions of capacitive sensors in which the capacitance is changed by changes in the capacitors' effective dielectric constants. In FIG. 21A a dielectric slab 234, affixed at one end to structure in a conveyor belt, extends partway into a gap 236 between upper and lower fixed plates 238, 239. The permittivity of the slab 234 differs from that of air. The slab 234 is also made of a material with a high coefficient of thermal expansion. When the temperature rises, as in FIG. 21B, the slab 234 extends farther into the gap 236. The region in the gap 236 occupied by the dielectric slab 234 increases with temperature. That causes the capacitance to increase and the resonant frequency to decrease as the temperature increases. A similar effect is achieved in the versions shown in FIGS. 22A-23B. Instead of a dielectric material with a high coefficient of thermal expansion, a fixed-size dielectric slab 240 is attached to one end of a bimetallic strip 242. The other end of the strip 242 is affixed to belt structure. When the temperature increases, the bimetallic strip 242 bends, as shown in FIG. 22B, which pushes the dielectric slab 240 deeper into the gap 236. The capacitive sensor in FIGS. 23A-23B uses a similar fixed-size dielective slab 240. Instead of a bimetallic strip, it uses a pusher 244 and a pivot 230 and an arm 228 as in FIG. 20A to push the slab 240 farther into the gap 236 so that the dielectric material fills more of the gap to increase the effective permeability.

FIGS. 24A-26B show inductive temperature sensors whose inductances change because of temperature-induced changes in the effective permeability of inductors in L-C circuits due to the number of windings encircling the cores. FIG. 24A shows an inductor coil 246 with a ferrite core 248 or a core made of another material extending through the center of the coil a first distance. The core 248 is made of a material also having a high coefficient of thermal expansion. When the temperature rises, as in FIG. 24B, the core 248 expands to extend farther into the coil 246 and link more of the coil's turns. The effective permeability and the inductance increase, and the resonant frequency of an L-C circuit including the coil 246 and a fixed capacitor decreases. The versions in FIGS. 25A-25B use a bimetallic strip 250 to push a fixed-length core 252 farther into the coil 246, as shown in FIG. 25B. In FIGS. 26A-26B the fixed-length core 252 is pushed by a pivotable arm 228 urged by a pusher 244 made of a material with a high coefficient of thermal expansion farther into the inductive coil 246 to change its inductance as a function of temperature.

FIGS. 27A-28B show inductive temperature sensors that use materials having high coefficients of thermal expansion to change the shapes of inductive coils. In FIG. 27A, an inductive coil 254 is wound around a core 256. The core is made of a material having a high coefficient of thermal expansion so that, when the temperature increases as in FIG. 27B, the core 256 expands radially and increases the diameter of the coil 254, which increases the coil's inductance and lowers the resonant frequency. In FIGS. 28A-28B an inductive coil 258 is attached at two points by arms 260, 261 to a slab 262 made of a material having a high coefficient of thermal expansion. As shown in FIG. 28B, the slab 262 elongates as the temperature increases. The elongating slab 262 draws the arms 260, 261 apart and lengthens the coil 258, which decreases the coil's inductance and increases the resonant frequency.

Inductive pressure sensors shown in FIGS. 29A-30B operate analogously to the temperature sensors of FIGS. 27A-29B. In FIGS. 29A-29B a coil 264 is wound around a closed, flexible pressure chamber 266 filled with a gas. When the external ambient pressure falls, as in FIG. 29B, the flexible chamber expands radially and increases the diameter and cross-sectional area of the coil 264, which increases the coil's inductance. In FIG. 30A the slab 262 of FIG. 28A is replaced by a gas-filled, expandable pressure chamber 268. The expansion of the chamber 268 with a falling external pressure elongates a coil 270 as in FIG. 30B and decreases its inductance.

Figure 33A:
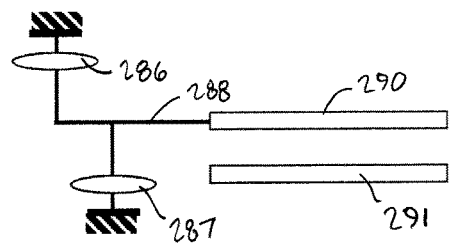
Figure 33B:
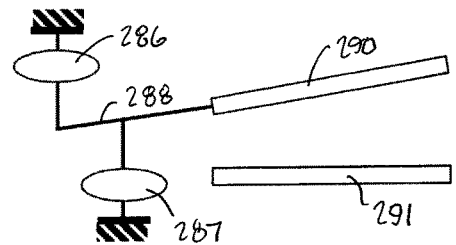

Various capacitive pressure sensors are shown in FIGS. 31A-33B. A fixed lower plate 272 is separated from a flexible upper plate 273 by a wall 274 forming a sealed chamber 276 with the plates. As shown in FIG. 31B, when the external pressure decreases, gas in the chamber 276 pushes the flexible upper plate 273 outward away from the fixed lower plate 272, which lowers the capacitance and increases the resonant frequency. In FIGS. 32A-32B the expansion of a gas in a closed chamber 278 pivots an arm 280 about a pivot 282 to separate plates 284, 285 of a capacitor as the external pressure decreases. The separation of the plates decreases the capacitance. FIGS. 33A-33B depict another version using two expandable pressure chambers 286, 287 attached to a linkage 288. The linkage 288 is attached to an upper plate 290 of a capacitive sensor. Dips in the external pressure, as in FIG. 33B, cause the pressure chambers 286, 287 to expand and pivot the linkage 288 to separate the top plate 290 from a fixed lower plate 291. The increased plate separation decreases the capacitance.

The sensors shown in FIGS. 34A-37B sense changes in ambient humidity. The capacitive sensor of FIGS. 34A-34B comprises two parallel plates 292, 293 separated by a separator 294 made of a hygroscopic material. The hygroscopic separator 294 expands with increasing humidity as shown in FIG. 34B. The expansion increases the separation between the plates, which decreases the capacitance and increases the resonant frequency. The sensor may also be used to detect spillage of wet materials. The capacitive humidity sensor of FIGS. 35A-35B operates like the capacitive temperature sensor of FIGS. 20A-20B, except that the pusher 296 is made of a hygroscopic material rather than a material with a high coefficient of thermal expansion. Increases in humidity cause the pusher 296 to elongate and separate the plates 298, 299 to decrease the capacitance. The inductive humidity sensors shown in FIGS. 36A-37B operate in the same way as the temperature sensors of FIGS. 27A-28B except that the materials made of high coefficients of thermal expansion are replaced by hygroscopic materials that expand with increased humidity. The expansion changes the inductance of the coil by changing its length (FIG. 37B) or its diameter (FIG. 36B).

FIGS. 38A-38B show an inductive sensor that detects changes in humidity or spillage. A coil 300 has a core 302 made of a hygroscopic material. An increase in humidity in the presence of spillage causes the core 302 to elongate as in FIG. 38B, which increases the coil's inductance.

FIGS. 39A-39B show a capacitive spillage sensor comprising two plates 304, 305 having a dielectric slab 306 in a portion of a gap 308 between the plates. The remainder of the gap 308 is filled with air in FIG. 39A. When a liquid leaks into the sensor, the liquid 310 displaces the air in a portion of the gap 308. Because the dielectric constant of the spillage differs from that of air, the effective permittivity of the capacitor formed by the two plates changes. The change in permittivity with spillage changes the capacitance and the resonant frequency. The two plates 304, 305 are shown oblique to each other, diverging from first ends of the plates to second ends, with the dielectric slab 306 in the narrowest portion of the gap 308 between the first ends of the plates. Spilled liquid tends to collect against the dielectric slab 306 by capillary action. In that way the spillage has a greater effect because it collects where the gap spacing is also smaller. But the plates can be parallel and still provide effective detection of spillage.

In all these examples of sensing elements, except the one represented by FIGS. 39A-39B, a force changes the orientation, dimensions (i.e., size or shape), permeability, or permittivity of a passive component—an inductor or a capacitor—in a resonant L-C circuit. Any of these changes also changes the inductance or capacitance and thus the resonant frequency of the resonant circuit. So all those sensing elements may be considered to be force-sensitive elements. The change in the resonant frequency is functionally related to the change in the force. And the force is caused by the weight of an article on the belt, a change in temperature, a change in ambient pressure, a change in humidity, or spillage onto the belt. But those of ordinary skill in the art can appreciate that similar techniques to change the inductance or capacitance of a circuit element can be used to detect other changing conditions affecting a conveyor belt.

Although the weighing system has been described in detail with reference to a few versions, other versions are possible. For example, the conveyor belt need not be a modular plastic conveyor belt. It could be a flat belt or a slat conveyor, for instance. As another example, visioning algorithms and detectable markers on the belt other than those described could be used by the vision system to identify individual articles and the load cells underlying them. Furthermore, some of the active components that make up the activation and measurement circuits described as external to the belt could instead be embedded in the belt with couplers coupling the output from the belt. In such an arrangement, the active components would be powered by a belt-embedded power source, such as a battery, a storage capacitor, or an energy harvester, or through inductive coupling from a source external to the belt. And techniques other than resonant techniques can be used to determine changes in inductance or capacitance due to belt deflections. So, as these few examples suggest, the scope of the claims is not meant to be limited to the details of the exemplary versions.

What is claimed is:

1. A conveyor belt comprising:
an endless belt body;
a plurality of resonant circuits disposed at sensor positions in the endless belt body, each of the resonant circuits including:
an inductor; and
a capacitor connected to the inductor to form the resonant circuit with a resonant frequency determined by the inductance of the inductor and the capacitance of the capacitor;
a plurality of capacitor plates, wherein each of the resonant circuits is connected to one or more capacitor plates to capacitively couple the resonant circuit through one or more stationary capacitor plates external to the conveyor belt;
wherein at least one of the inductance of the inductor and the capacitance of the capacitor is varied by a varying condition affecting the conveyor belt.

2. A conveyor belt as in claim 1 wherein the inductor has a fixed inductance and is arranged to inductively couple the resonant circuit to a stationary activation circuit external to the conveyor belt.

3. A conveyor belt as in claim 1 wherein the capacitor has a fixed capacitance and is arranged to capacitively couple the resonant circuit to a stationary activation circuit external to the conveyor belt.

4. A conveyor belt as in claim 1 further comprising a plurality of coupling coils each connected to one of the resonant circuits to inductively couple the resonant circuit to a stationary activation circuit external to the conveyor belt.

5. A conveyor belt as in claim 1 wherein the inductance of the inductor or the capacitance of the capacitor in each of the resonant circuits is varied by changes in the dimensions of the inductor or the capacitor caused by the varying condition affecting the conveyor belt.

6. A conveyor belt as in claim 1 wherein the inductor in each of the resonant circuits has coil windings and a core inside the coil windings and wherein the varying condition affecting the conveyor belt causes changes in the length of the core inside the windings, which changes the inductance of the inductor.

7. A conveyor belt as in claim 1 wherein the capacitor in each of the resonant circuits has a first plate and a second plate separated from the first plate by a gap and a dielectric slab in a portion of the gap and wherein the varying condition affecting the conveyor belt causes changes in the dimensions of the dielectric slab and the portion of the gap occupied by the dielectric slab, which changes the capacitance of the capacitor.

8. A conveyor belt as in claim 7 wherein the first plate and the second plate diverge from first ends of the plates to opposite second ends so that the gap is wider at the second end than at the first end and wherein the dielectric slab is disposed in a portion of the gap between the first ends of the plates and wherein the remaining portion of the gap from the dielectric slab to the second ends of the plates is an air gap into which spilled liquids can collect and change the effective permittivity and the capacitance of the capacitor.

9. A conveyor belt as in claim 1 wherein the varying condition affecting the conveyor belt is selected from the group consisting of: weight of articles conveyed on the conveyor belt, temperature of the conveyor belt, ambient pressure on the conveyor belt, ambient humidity, and liquid spillage onto the conveyor belt.

10. A conveyor-belt measuring system comprising:
a conveyor belt including:
a plurality of resonant circuits disposed at sensor positions in the conveyor belt, each of the resonant circuits having a resonant frequency and including:
an inductor; and
a capacitor connected to the inductor to form the resonant circuit with a resonant frequency determined by the inductance of the inductor and the capacitance of the capacitor;
wherein either the inductor is a sensing element whose inductance is varied by a varying condition affecting the conveyor belt or the capacitor is the sensing element whose capacitance is varied by the varying condition affecting the conveyor belt;
wherein the variation of the inductance or the capacitance of the sensing element changes the resonant frequency as a function of the condition affecting the conveyor belt;
a coupling element connected to the sensing element;
at least one stationary measurement circuit external to the conveyor belt and including:
a frequency detector; and
a stationary coupling element coacting with the coupling elements in the conveyor belt as they pass close to the stationary coupling element to couple the resonant circuits to the frequency detector;
wherein the frequency detector measures changes in the resonant frequency of the resonant circuits caused by the condition affecting the conveyor belt.

11. A conveyor-belt measuring system as in claim 10 wherein the coupling element in the conveyor belt and the stationary coupling element provide one or the other of inductive coupling and capacitive coupling.

12. A conveyor-belt measuring system as in claim 10 wherein the coupling element in the conveyor belt includes a first plate of a capacitor and the stationary coupling element includes a second plate of the capacitor formed as the first plate in the conveyor belt passes closely by the second plate.

13. A conveyor-belt measuring system as in claim 10 wherein the coupling element in the conveyor belt is a spring-loaded plate and the stationary coupling element includes a pair of spaced apart plates forming separate capacitors with the spring-loaded plate in the conveyor belt.

14. A conveyor-belt measuring system as in claim 10 wherein the at least one stationary measurement circuit includes a differentiating amplifier connected between the stationary coupling element and the frequency detector.

15. A conveyor-belt measuring system as in claim 10 wherein the at least one stationary measurement circuit includes an oscillator oscillating at a nominal resonant frequency and connected between the stationary coupling element and the frequency detector, wherein changes in the resonant frequency of the resonant circuits change the frequency of the oscillator from the nominal resonant frequency as the resonant circuits pass the at least one stationary measurement circuit.

16. A conveyor-belt measuring system as in claim 10 wherein the condition affecting the conveyor belt is selected from the group consisting of: weight of articles conveyed on the conveyor belt, temperature of the conveyor belt, ambient pressure on the conveyor belt, ambient humidity, and liquid spillage onto the conveyor belt.

17. A conveyor-belt measuring system as in claim 10 comprising a controller and wherein the frequency detector determines the frequencies of the resonant circuits and sends the frequencies to the controller.

18. A conveyor-belt measuring system as in claim 17 further comprising an array of stationary measurement circuits under the conveyor belt across its width and wherein the sensing elements sense the weight of articles conveyed on the conveyor belt and change the resonant frequencies of the resonant circuits accordingly and wherein the controller computes the position, the skew, or the center of gravity of each of the conveyed articles from the weights determined from the array of stationary measurement circuits.

19. A conveyor-belt measuring system comprising:
 a conveyor belt including:
  a plurality of sensing elements disposed at sensor positions in the conveyor belt, wherein an electrical property of each of the sensing elements is changed by a condition affecting the conveyor belt;
 at least one stationary measurement circuit external to the conveyor belt and including:
  a frequency detector; and
  a stationary coupling element coupling the at least one stationary measurement circuit to the plurality of sensing elements in the conveyor belt as they pass close to the stationary coupling element;
 wherein each of the sensing elements forms part of a resonant circuit having a resonant frequency that depends on the electrical property of sensing element;
 wherein the frequency detector measures changes in the resonant frequency of the resonant circuit due to changes in the electrical property of the sensing element caused by the condition affecting the conveyor belt;
 wherein the sensing element is an inductor or a capacitor and the electrical property is the inductance of the inductor or the capacitance of the capacitor.

20. A conveyor-belt measuring system as in claim 19 further comprising a plurality of coupling elements in the conveyor belt, each connected to a respective one of the sensing elements for coupling the sensing element to the at least one stationary measurement circuit through the stationary coupling element.

21. A conveyor-belt measuring system as in claim 19 wherein each of the sensing elements is also a coupling element coupling to the at least one stationary measurement circuit through the stationary coupling element.

22. A conveyor-belt measuring system as in claim 19 wherein the resonant circuit is disposed in the conveyor belt.

23. A conveyor-belt measuring system as in claim 19 wherein the resonant circuit is distributed between the conveyor belt and the at least one stationary measurement circuit.

24. A conveyor-belt measuring system as in claim 19 wherein the condition affecting the conveyor belt is selected from the group consisting of: weight of articles conveyed on the conveyor belt, temperature of the conveyor belt, ambient pressure on the conveyor belt, ambient humidity, and liquid spillage onto the conveyor belt.

* * * * *